United States Patent
Lal et al.

(10) Patent No.: US 8,478,378 B2
(45) Date of Patent: Jul. 2, 2013

(54) DEVICES, SYSTEMS AND METHODS TO DETECT ENDOTHELIALIZATION OF IMPLANTABLE MEDICAL DEVICES

(75) Inventors: Ratnesh Lal, Goleta, CA (US); Neeraj Jolly, Chicago, IL (US); Sungho Jin, San Diego, CA (US); Jaishankar Raman, Chicago, IL (US)

(73) Assignee: The Regents of the University of California, Oakland, CA (US)

( * ) Notice: Subject to any disclaimer, the term of this patent is extended or adjusted under 35 U.S.C. 154(b) by 1242 days.

(21) Appl. No.: 12/203,667

(22) Filed: Sep. 3, 2008

(65) Prior Publication Data

US 2009/0062900 A1 Mar. 5, 2009

Related U.S. Application Data

(60) Provisional application No. 60/969,834, filed on Sep. 4, 2007, provisional application No. 60/969,810, filed on Sep. 4, 2007, provisional application No. 60/969,801, filed on Sep. 4, 2007.

(51) Int. Cl.
*A61B 5/04* (2006.01)
*A61B 5/00* (2006.01)

(52) U.S. Cl.
USPC ........... 600/381; 600/325; 600/327; 600/372; 600/375; 600/377; 600/505; 600/506

(58) Field of Classification Search
USPC ............... 600/300, 345, 504, 505, 506, 325, 600/327, 372, 375, 377, 381
See application file for complete search history.

(56) References Cited

U.S. PATENT DOCUMENTS

| | | | |
|---|---|---|---|
| 5,421,955 A * | 6/1995 | Lau et al. | 216/48 |
| 6,053,873 A | 4/2000 | Govari et al. | |
| 6,564,100 B2 | 5/2003 | Warren et al. | |
| 7,016,732 B2 | 3/2006 | Warren et al. | |
| 7,769,420 B2 * | 8/2010 | Silver et al. | 600/345 |
| 2007/0219623 A1 | 9/2007 | Palmaz | |
| 2008/0011058 A1 * | 1/2008 | Lal et al. | 73/54.23 |

FOREIGN PATENT DOCUMENTS

WO WO/2007/109323 A2 9/2007

OTHER PUBLICATIONS

Gibson et al. (How RFID Works. http ://electronics.howstuffworks.com/rfid5 .htm. (2002?).*
Brammer, K.S. et al. "Enhanced Cellular Mobility Guided by TiO2 Nanotube Surfaces", Nano Letters, vol. 8, No. 3, pp. 876-893 (2008).
Quist, A. et al. "Piezoresistive Cantilever Based Nanoflow and Viscosity Sensor for Microchannels", Lab. Chip, vol. 6, pp. 1450-1454 (2006).

* cited by examiner

*Primary Examiner* — Gail R Gabel
(74) *Attorney, Agent, or Firm* — Gregory P. Einhorn; Gavrilovich, Dodd & Lindsey LLP

(57) ABSTRACT

An implantable medical device including a radially-expandable body and an attached detection device. The detection device includes a sensor positioned on a surface of the radially-expandable body and configured to detect endothelialization of the surface. The detection device also includes a transmitter and a receiver. Systems incorporating the implantable medical device and methods of using the device are also disclosed.

13 Claims, 7 Drawing Sheets

US 8,478,378 B2

DEVICES, SYSTEMS AND METHODS TO DETECT ENDOTHELIALIZATION OF IMPLANTABLE MEDICAL DEVICES

RELATED APPLICATIONS

This non-provisional patent application claims priority to U.S. Provisional Patent Application Nos. 60/969,834, 60/969,810 and 60,969,801, filed Sep. 4, 2007, the contents of all of which are incorporated by reference in their entirety.

FIELD OF THE INVENTION

This invention relates generally to the field of implantable medical devices and in particular to implantable vascular stents incorporating a device for the detection of endothelialization of the vascular stent.

BACKGROUND OF THE INVENTION

Coronary artery disease is a condition that causes narrowing of the coronary arteries, reducing blood flow to the heart muscle. Severe cases can result in a heart attack. A common treatment for coronary artery disease involves balloon angioplasty with or without stenting.

Angioplasty is a medical procedure in which a balloon is used to open these narrowed or blocked blood vessels of the heart. A catheter with a deflated balloon on its tip is passed into the narrowed artery segment, the balloon is inflated and the narrowed segment widened. Then the balloon is deflated and the catheter is removed. This is also known as Percutaneous Transluminal Coronary Angioplasty (PTCA).

About one-third of patients who undergo PTCA have restenosis of the widened segment within about six months of the procedure. In order to prevent restenosis, a metallic stent is commonly placed at the site of angioplasty (stenting). A stent is a metallic wire mesh tube that helps to keep open an artery after it is widened using angioplasty. Some of these stents are coated with a medication that is released locally into the arterial wall to further reduce the chances of arterial narrowing. These stents are called drug-eluting stents (DES), and are the most common variety of stents currently used. Examples of such medications include paclitaxel (TAXOL®) and other taxane derivatives, Biolimus A7, BIOLIMUS A9™, everolimus, sirolimus (rapamycin), pimecrolimus, or any other members of the -olimus family. Desirably, the medication is released within the body at a reproducible and predictable fashion so as to optimize the benefit of the medication to the patient over the desired period of time.

Approximately one million coronary stent procedures are performed annually in the United States. Once implanted into the heart artery, the inner lining of the artery grows over the metallic stent struts by a process called endothelialization. Through endothelialization the stent eventually becomes a part of the vessel wall.

A rare but potentially fatal complication associated with implantation of a DES in the coronary artery is the formation of a blood clot (thrombus) inside the blood vessel at the stented site. This can happen months or even years after the procedure, and is called "late stent thrombosis" (LST). LST is a vexing clinical problem (see W. H. Maisel, "Unanswered Questions—Drug-eluting Stents and the Risk of Late Thrombosis", New England Journal of Medicine, vol. 356, page 981-984 (2007)), and is associated with high rates of heart attack and death.

Understanding its pathogenesis and its prevention, therefore, is of primary importance to management of patients with coronary artery disease. Delayed or late stent thrombosis is related to delayed endothelialization of the intra-coronary stent (see A. V. Finn, M. Joner, G. Nakazawa, et al., "Pathological Correlates of Late Drug-Eluting Stent Thrombosis: Strut Coverage as a Marker of Endothelialization". Circulation Vol. 115, page 1-7 (2007). Needed in the art are devices, systems and methods to detect and monitor endothelialization of intravascular stent devices.

SUMMARY

One aspect of the present invention provides an implantable medical device. In one embodiment, the implantable medical device includes a detection device attached to a radially-expandable body. The detection device includes a sensor positioned on a surface of the radially-expandable body and configured to detect endothelialization of the surface. The detection device also includes a transmitter coupled to the sensor and configured to transmit a signal from the sensor and a receiver coupled to the sensor and the radio transmitter and configured to provide electrical power to the detection device from a radio frequency received from an external power source. In one embodiment, the transmitter is a radio frequency transmitter. In another embodiment, the detection device is positioned on the luminal surface of the radially-expandable body.

In one embodiment, the sensor is a piezoresistive cantilever sensor. In another embodiment, the sensor includes at least two electrodes positioned apart on a surface of the radially-expandable body. The signal from the sensor is dependent upon the electrical resistance or electrical capacitance between the two electrodes.

In another embodiment, the detection device includes at least two sensors positioned on a surface of the radially-expandable body and the transmitter is configured to transmit a signal from each of the sensors. In one embodiment, at least one of the two sensors is a piezoresistive cantilever sensor.

Another aspect provides a system for detecting endothelialization of a surface of a medical device. In one embodiment, the system includes a detection device attached to the medical device. The detection device includes a sensor positioned on a surface of the medical device and configured to detect endothelialization of the surface. The detection device also includes a transmitter coupled to the sensor and configured to transmit a signal from the sensor and a receiver coupled to the sensor and the radio transmitter. The system also includes a base unit including a base unit transmitter configured to transmit a signal to the receiver, a base unit receiver configured to receive a signal from the transmitter, and a processor configured to process the received signal from the transmitter.

Another aspect provides a method for determining endothelialization of a surface of a medical device implanted within a vascular system of a patient. In one embodiment, the method includes transmitting a radio frequency signal from a base unit transmitter to a detection device attached to the medical device. The detection device includes (i) a sensor positioned on a surface of the medical device and configured to generate a sensor signal indicative of the presence of or degree of endothelialization of the surface, (ii) a detector transmitter coupled to the sensor and configured to transmit a signal indicative of the sensor signal to a base unit receiver positioned outside the patient; and (iii) a detector receiver coupled to the sensor and the detector transmitter and configured to receive the signal from the base unit transmitter. The method also includes detecting the signal from the detector transmitter, where the signal from the detector transmitter is transmitted in response to the radio frequency signal, and processing the signal from the detector transmitter to determine the presence of or degree of endothelialization of the surface.

In one embodiment, the medical device is a vascular stent including a radially-expandable body and the surface is a luminal surface of the radially-expandable body. In another embodiment, the radio frequency signal is generated by a base unit positioned outside the patient.

In one embodiment, the endothelialization of the surface of the medical device is determined at least one month following implantation of the medical device in the patient. In another embodiment, the endothelialization of the surface of the medical device is determined at multiple times and is indicative of delayed endothelialization of the medical device.

In yet another embodiment, the detection device comprises at least two sensors positioned on a surface of the radially-expandable body and configured to detect endothelialization of the surface and the detector transmitter transmits a signal indicative of a sensor signal from each of the sensors.

In another embodiment, the sensor is configured to detect an endothelialization layer having a thickness of between 10 microns and 200 microns.

DESCRIPTION OF THE ILLUSTRATIVE EMBODIMENTS

Definitions

Figure 1A:
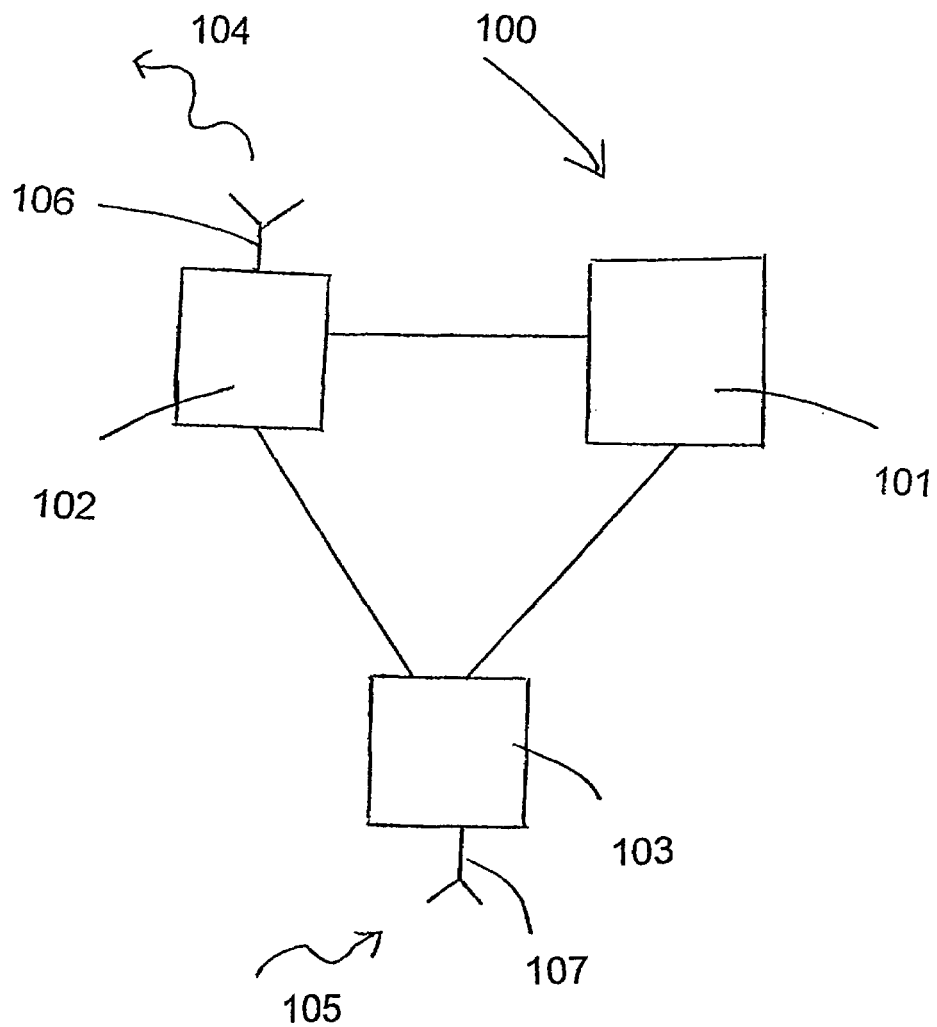
FIG. 1(a) is a schematic diagram illustrating one embodiment of the components of a detection device for detecting endothelialization.
Figure 1B:
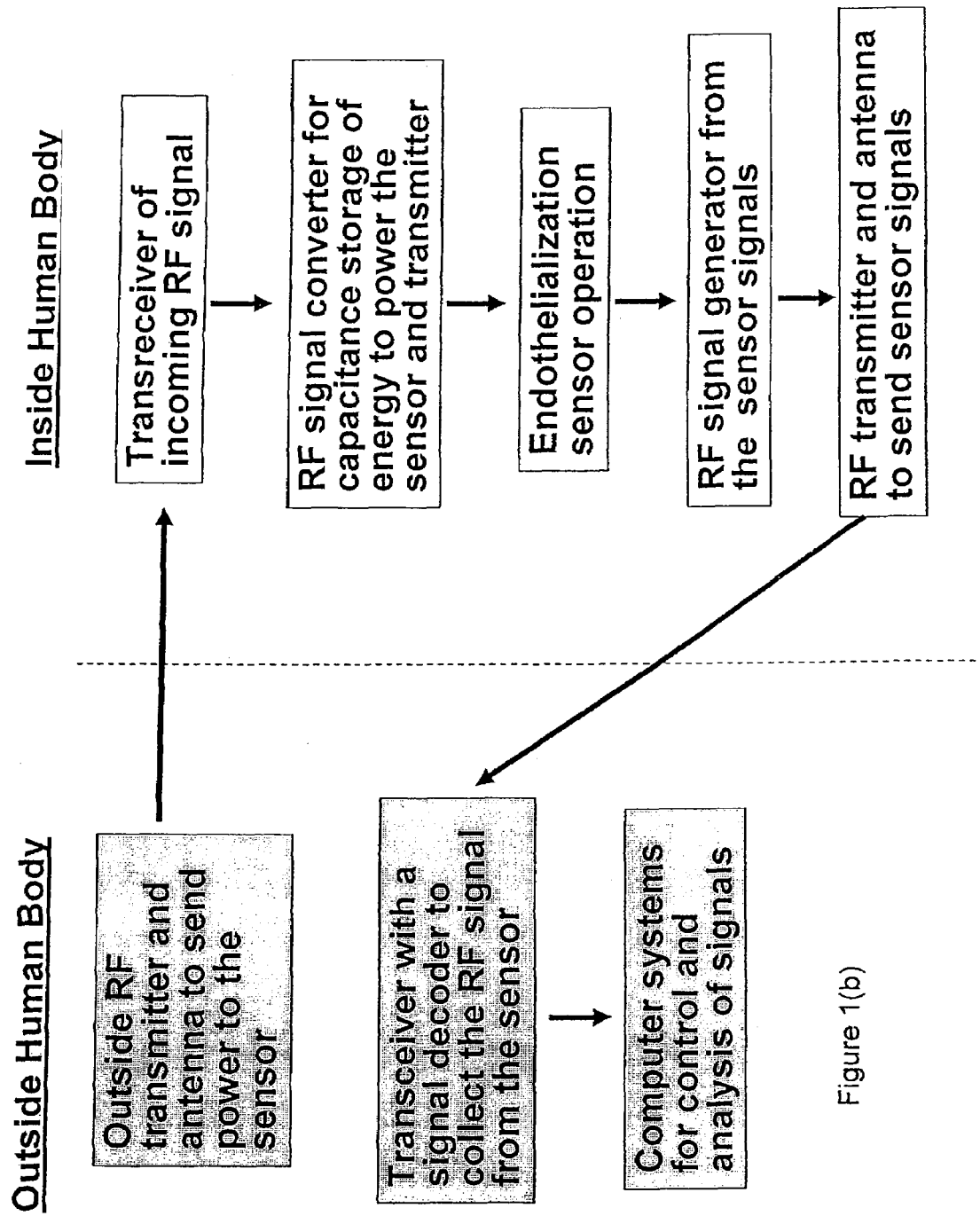
FIG. 1(b) is a flow diagram illustrating the process of detecting endothelialization.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

As used in the specification and the appended claims, the singular forms "a," "an" and "the" include plural referents unless the context clearly dictates otherwise. Thus, for example, reference to "a physical or biological property" includes embodiments comprising a plurality of physical or biological properties, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Subject" includes, but is not limited to animals comprising vascular structures. The subject may be a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The term "implantable" refers to an ability of a medical device to be positioned, partially or wholly, at a location within a body, such as within a body vessel. Furthermore, the terms "implantation" and "implanted" refer to the positioning of a medical device at a location, partially or wholly, within a body, such as within a body vessel.

A "biocompatible" material is a material that is compatible with living tissue or a living system by not being toxic or injurious and not causing immunological rejection.

The term "luminal surface," as used herein, refers to the portion of the surface area of a medical device defining at least a portion of an interior lumen. Conversely, the term "abluminal surface," as used herein, refers to portions of the surface area of a medical device that do not define at least a portion of an interior lumen. For example, where the medical device may be a vascular stent having a cylindrical frame formed from a plurality of interconnected struts and bends defining a cylindrical lumen, the abluminal surface can include the exterior surface, sides and edges of the struts and bends, while the luminal surface can include the interior surface of the struts and bends.

Medical Devices Incorporating a Device for the Detection of Endothelialization

One aspect of the present embodiments provides a medical device including a detection device enabling the presence or degree of endothelialization on the surface of the medical device to be determined while the medical device is implanted within the vascular system of a patient. In one embodiment, the medical device is an expandable medical device. In another embodiment, the medical device is a vascular stent, for example a coronary stent or a stent for placement in the peripheral vascular system. In some embodiments a stent may be placed in an artery, while in other embodiments a stent may be placed in a vein.

Typically, vascular stents are cylindrical in shape, and are manufactured in a number of diameters and lengths depending on the application in question. They typically consist of cross-hatched, braided or interconnecting rows of metal struts that are assembled into a tube-like structure. When unexpanded, they are small enough to fit through the channel of a catheter for delivery of the stent. When expanded, the stent contacts the wall of the vessel and provides support for the vessel wall. Stents may be either self expanding or may be expanded by a balloon.

In some embodiments, the detection devices, including the sensors, are constructed to resist a force of at least 30 atmospheres in order to endure the force of balloon expansion during stent implantation. The sensors can be biocompatible and non-toxic. In some embodiments, the sensors are made of implantable medical and surgical materials well known to those skilled in the art. The sensors can have desirable mechanical toughness so that their parts do not inadvertently break off during balloon expansion to avoid distal embolization.

Expandable Stents

The stent may be self-expanding or balloon-expandable and may be a bifurcated stent, a coronary vascular stent or a stent designed for placement in the peripheral vascular system. Some exemplary stents are disclosed in U.S. Pat. No. 5,292,331 to Boneau, U.S. Pat. No. 6,090,127 to Globerman, U.S. Pat. No. 5,133,732 to Wiktor, and U.S. Pat. No. 4,739,762 to Palmaz, U.S. Pat. No. 5,421,955 to Lau, the contents of which are incorporated by reference. Commercially available stents include CYPHER® (Johnson & Johnson), EXPRESS™ stent (Boston Scientific), LIBERTE™ (Boston Scientific), TAXUS® Express™ (Boston Scientific), XIENCE V™ (Abbott Lavoratories).

Typically, coronary stents are about 10 mm to 30 mm in length and designed to expand to a diameter of about 2 mm to about 5 mm when inserted into the vascular system of the patient.

These stent dimensions are, of course, applicable to exemplary stents employed in the coronary arteries. Structures such as stents or catheter portions intended to be employed at other sites in the patient, such as in the aorta and the neck will have different dimensions more suited to such use. For example, aortic stents may have diameters of about 25 mm and lengths of about 100 mm or longer.

The structure of the stent is composed of a base material suitable for the intended use of the structure. The base material is preferably biocompatible, although cytotoxic or other poisonous base materials may be employed if they are adequately isolated from the patient. Such incompatible materials may be useful in, for example, radiation treatments in which a radioactive material is positioned by catheter in or close to the specific tissues to be treated. Under most circumstances, however, the base material of the structure should be biocompatible.

A variety of conventional materials can be employed as the base material. Some materials may be more useful for structures other than the coronary stent exemplifying the structure. The base material may be either elastic or inelastic, depending upon the flexibility or elasticity of the polymer layers to be applied over it. The base material may be either biodegradable or non-biodegradable, and a variety of biodegradable polymers are known. Moreover, some bioactive agents have sufficient strength to serve as the base material of some useful structures, even if not especially useful in the exemplary coronary stent.

The materials used in stents or other medical devices of the invention may be selected from a well-known list of suitable metals and polymeric materials appropriate for the particular application, depending on necessary characteristics that are required (self-expansion, high radial force, collapsibility, etc.). Suitable metals or metal alloys include stainless steels (e.g., 316, 316L or 304), nickel-titanium alloys including shape memory or superelastic types (e.g., NITINOL™); INCONEL™; noble metals including copper, silver, gold, platinum, paladium and iridium; refractory metals including Molybdenum, Tungsten, Tantalum, Titanium, Rhenium, or Niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials, including magnesium; or other biocompatible metals and/or alloys thereof.

In one embodiment, the stent includes a self-expanding nickel titanium (NiTi) alloy material. The nickel titanium alloy sold under the trade name NITINOL™ is a suitable self-expanding material that can be deformed by collapsing the frame and creating stress which causes the NiTi to reversibly change to the martensitic phase. The frame can be restrained in the deformed condition inside a delivery sheath typically to facilitate the insertion into a patient's body, with such deformation causing the isothermal phase transformation. Once within the body lumen, the restraint on the frame can be removed, thereby reducing the stress thereon so that the superelastic frame returns towards its original undeformed shape through isothermal transformation back to the austenitic phase. Other shape memory materials may also be utilized, such as, but not limited to, irradiated memory polymers such as autocrosslinkable high density polyethylene (HDPEX).

Some embodiments provide medical devices that are not self-expanding, or that do not comprise superelastic materials. For example, in other embodiments, the medical device can comprise silicon-carbide (SiC). For example, published U.S. Patent Application Number US2004/034409 to Hueblein et al, published on Feb. 14, 2004 and incorporated in its entirety herein by reference, discloses various suitable materials and configurations.

Other suitable materials used in the medical device include carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; polylactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these.

The medical device may be deployed according to conventional methodology, such as by an inflatable balloon catheter, by a self-deployment mechanism (after release from a catheter), or by other appropriate means. The medical device may be formed through various methods, such as welding, laser cutting, or molding, or it may consist of filaments or fibers that are wound or braided together to form a continuous structure.

Attachment of the Detection Device to the Implantable Medical Device

The detection device may be attached to the implantable medical device by any suitable method. For example the detection device may be attached to a strut of an expandable stent using an adhesive, welding, soldering or fasteners. In certain embodiments the detection device is attached directly to the surface of a strut. In other embodiments, a layer of insulating material is coated onto a portion of the surface of the stent and the detection device attached to this insulating layer. The detection device may be attached to any surface of the implantable device. In one embodiment, the detection device is attached to a luminal surface of the implantable device.

In yet other embodiments, the detection device is situated in a hole or well formed in the material of the stent. For example, the detection device may be contained in a hole or well formed in a strut of an expandable stent or a hole or well formed at the junction of two or more struts.

In certain embodiments, at least a portion of the detection device or the entire detection device is covered with an insulating layer. In one embodiment, the insulating layer includes a polymer. In such embodiments, a portion of the sensor device may be masked before the application of this insulating layer. After application of the insulating layer, the mask is removed so that the portion of the sensor is not covered by an insulating layer.

In one embodiment, the sensor is less than 0.01 inch in width. In other embodiments, the sensor is smaller than 0.001 inch wide and 0.05 inch long. When the stent is collapsed and later expanded, there will be plastic deformation which can damage or crack the sensors. In certain embodiments, portions of the stent wire struts are made thicker to increase the strength of the portion plastically deformed. In other embodiments, portions of the stent that will contain the detector are subjected to plastic deformation to "work harden" a metal or metal alloy strut. In yet other embodiments, the stent is fabricated from thicker wire, for example 15 mil diameter mesh wire, instead of the typical 10 mil diameter wire.

In one embodiment, the stent is formed from 10 mil diameter Co—Cr stainless steel wires (also called MP 35N). On this 15 mil diameter wire mesh, some selected portions where we want to attach the sensors are be masked with, for example, a polymer or gold coat, and then the remaining stent wire sections chemically etched or ion etched to reduce the diameter to ~10 mil diameter. After dissolving away the mask, the 15 mil diameter portions are stamp-flattened using a specially configured cylindrical die to create a flat work-hardened portion for detector attachment.

Detection Device

FIG. 1(a) is a schematic diagram illustrating one embodiment of the components of a detection device for detecting endotheliatization of the surface of an implanted medical device. Detection device 100 includes sensor 101, which is operatively coupled to receiver 102. Transmitter 103 is operatively coupled to sensor 100 and receiver 102. Receiver 103 is configured to receive signal 105 via receiving aerial 107. In certain embodiments, signal 105 is a radio frequency (RF), thermal, light, or magnetic signal generated from outside the body of the patient. In one embodiment, signal 105 provides power for transmitter 102 and sensor 101, eliminating the need for an internal battery to be included as part of detection device 100.

In one embodiment, power for the detection device is supplied in the form of an electromagnetic signal from outside the patient's body, for example, a radio frequency signal. In another embodiment, magnetic induction can be employed and the energy so captured by a portion of the sensor circuit can be stored as a magnetic or capacitive energy which the detection device can use for sending measurement data to a receiver outside the patient's body. In other embodiments, a micro scale thermoelectric device can be used as a part of the detection device to capture a temperature differential near the stent created by infrared light heating from outside through the patient's body.

In one embodiment, sensor 100 is positioned on a surface of the implanted medical device and configured to detect endotheliatization of the surface. Sensor 100 is activated by signal 105 and generates a signal indicative of the presence or degree of endothelialization on the surface. Transmitter 102 is coupled to sensor 100 and configured to transmit sensor signal 104 from sensor 100 to a receiver outside the body of the patient.

Figure (b) illustrates one embodiment of the process of detecting endotheliatization of the surface of an implanted medical device. A radio frequency (RF) transmitter positioned outside the body of the patient transmits a signal that is detected by a receiver included in the detector (transreceiver) present on the implanted medical device. The RF signal is converted for capacitance storage of energy that is used to provide power for the sensor and the detector transmitter.

The sensor is activated by the power provided by the RF signal and provides a sensor signal indicative of the presence or absence of or degree of endotheliatization of the surface of the implanted device. The detector transmitter deceives the signal from the sensor and generates a RF signal indicative of the sensor signal.

The RF signal from the detector transmitter is received and decoded by a base unit receiver positioned outside the body of the patient. The base unit also includes a computer system that processes this signal and provides an output indicating the presence or absence of or degree of endotheliatization of the surface of the implanted device.

Sensors

Figure 2:
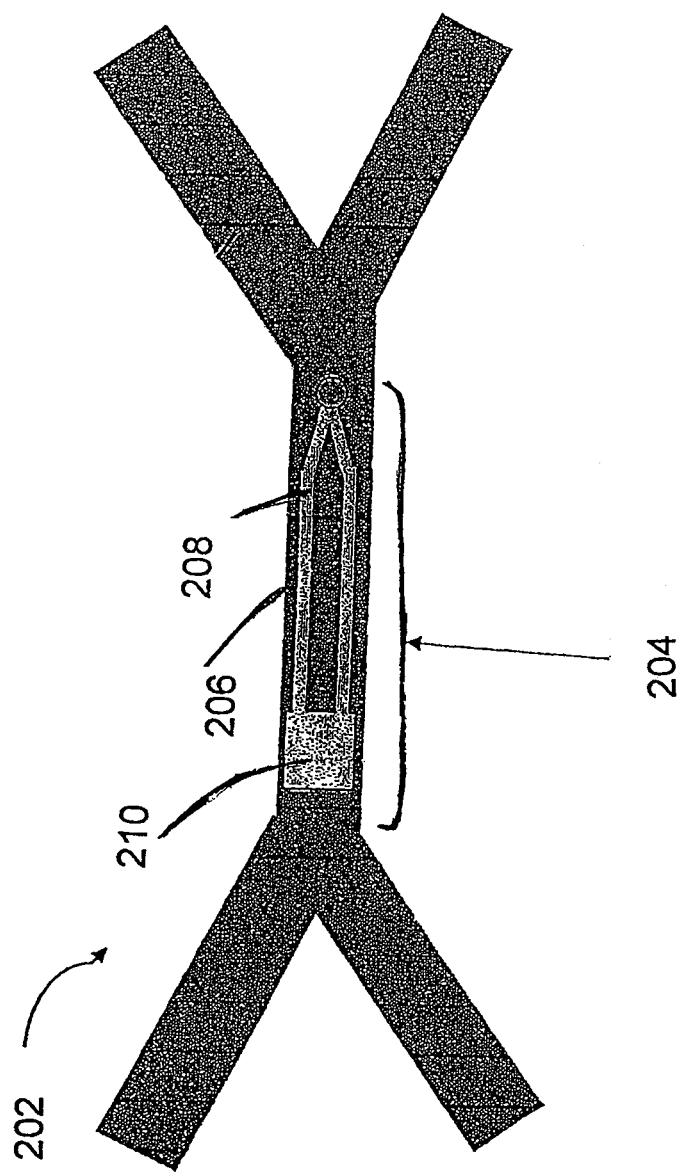
FIG. 2 is a schematic diagram illustrating a portion of the implanted stent 202 with a remote endothelialization detection device.

FIG. 2 is a schematic diagram illustrating a portion of the implanted stent 202 with a remote endothelialization detection device 204 in accordance with one embodiment. Detection device 204 includes endothelialization sensor 208, for example a piezoresistive cantilever sensor, and transmitter and detection components 210. Detection device is attached to strut 206 of stent 202. Sensor 208 is configured to detect endothelialization of the surface of strut 206.

The ability of a sensor to detect endothelialization of a surface can be determined using an in vitro technique to correlate changes in the signal from the sensor with independent measurements of cell growth. For example, cultured human coronary artery endothelial cells (HCAECs) can be grown on surfaces including the three major stent alloys: stainless steel 316L alloy, cobalt-chromium alloy, and NITINOL™. Typically, cells are grown in vitro at 37° C. at a medium pH of 7.40 to best mimic in vivo conditions. Growth parameters of the cells are then assessed by measuring, for example, the transendothelial resistance (TER) between cell membranes to determine the approximate distance between endothelial cells. A microscope can also be used to directly visualize HCAECs growing on the surfaces.

In one embodiment, the detection device includes a sensor allowing detection of an endothelialization layer having an average thickness of one endothelial cell. In other embodiments, the detection device includes a sensor allowing for detection of an endothelialization layer having an average thickness of 2, 5, 10, 15 or 20 endothelial cells. In yet other embodiments, the detection device allows for detection of an endothelialization layer having a thickness of between 10 microns and 20 microns, 20 microns and 50 microns, 50 microns and 100 microns, 100 microns and 200 microns, 10 microns and 200 microns, 10 microns and 100 microns, or 10 microns and 50 microns. In other embodiments, the detection device allows for detection of an endothelialization layer having a thickness of approximately 5 microns, 10 -microns, 20 microns, 50 microns, 100 microns, 150 microns or 200 microns. In yet other embodiments, the detection device allows for detection of an endothelialization layer having a thickness of greater than approximately 5 microns, 10 microns, 20 microns, 50 microns, 100 microns, 150 microns or 200 microns. In another embodiment, the detection device allows for detection of a endothelialization layer having a thickness of 100 microns or less.

Piezoresistive Cantilever Sensors

In one embodiment, the sensor is a piezoresistive cantilever sensor. Examples of piezoresistive cantilever sensors, including methods of manufacturing microcantilever devices, are described in U.S. Publication Number 2008/0011058A1, published Jan. 17, 2008, entitled "Piezoresistive Cantilever Based Nanoflow and Viscosity Sensor for Microchannels", the contents of which are incorporated by reference.

For example, microcantilever devices can be manufactured using a variety of microfabrication techniques, including by a combination of deposition (e.g. CVD) and micromachining (etching) methods. Devices of a size of approximately 265× 50 microns in length and 2.7 microns thick can be manufactured using a focused ion beam (FIB International, Santa Clara, Calif., USA)

Various deposition methods can be used to build up layers comprising the microcantilever devices of this invention. Such deposition methods include, but are not limited to chemical vapor deposition (CVD), plasma-assisted vapor deposition, and electron beam evaporation deposition, focused ion beam deposition, and the like.

Typically, a cantilever sensor includes a sensing tip attached to a piezoresistive element. The interactions of the sensor tip with sensor tip environment leads to physical alteration in the dimensions, such as the deflection, of the sensor. The sensor deflection is detected by the piezoresistive element. Such sensors can be fabricated to detect changes within a small volume, for example, within a small volume of fluid. In one embodiment, the cantilever sensor includes one lever of length less than 200 microns, 100 microns, 75 microns, or 50 microns. In other embodiments, the cantilever sensor includes one lever of length between 200 microns and 100 microns, between 100 microns and 75 microns, between 75 microns and 50 microns, or about 50 microns.

Figure 3:
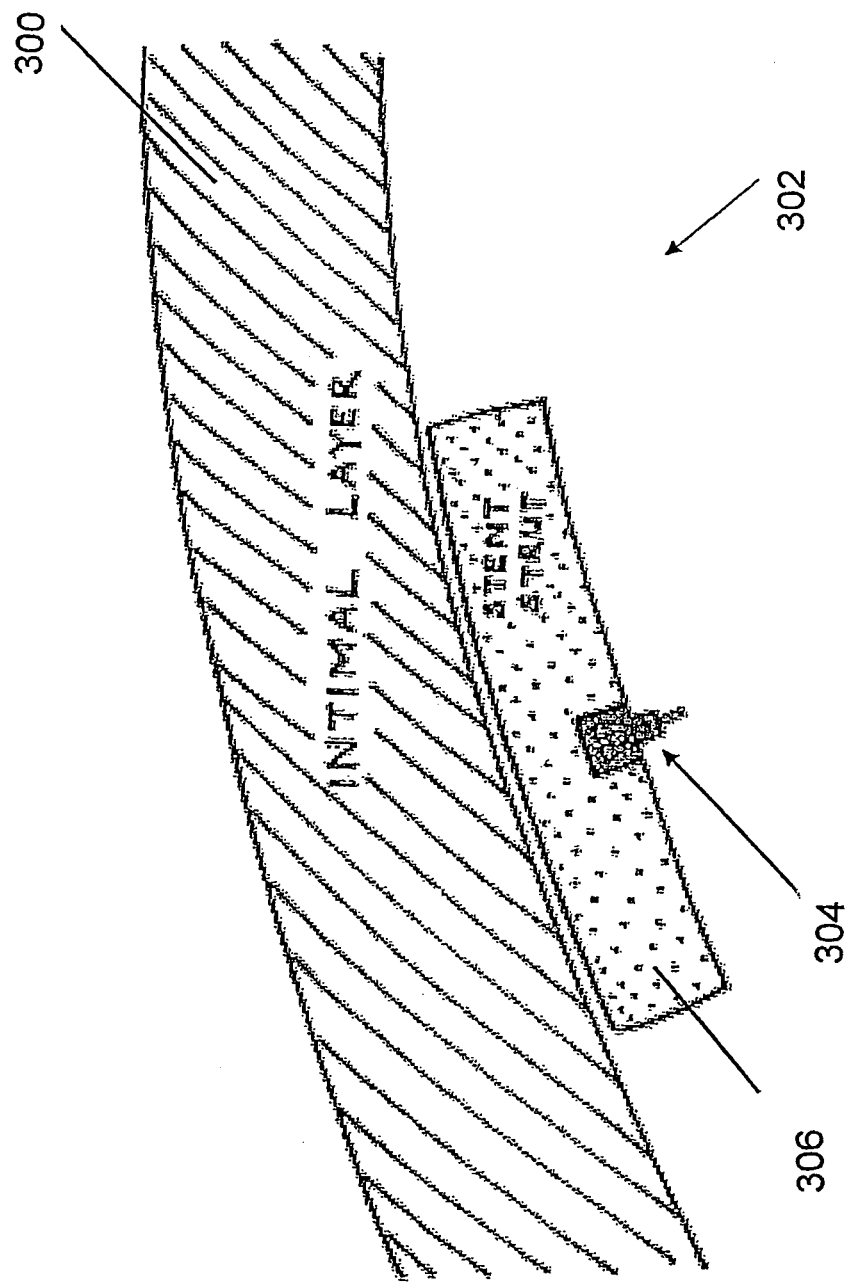
FIG. 3 is a schematic diagram illustrating a micro-cantilever sensor attached onto an implanted stent.

In one embodiment, as illustrated schematically in FIG. 3, a micro-cantilever sensor 304 can be attached onto the strut 306 of the implanted stent. The micro-cantilever sensor can be used to detect endothelialization by detecting changes in the interaction between the cantilever and blood flowing in the lumen 302, for example by detecting changes in pressure. For example, as endothelial cells grow over the stent strut, the cells can cover the cantilever of one or more sensor device positioned in association with the stent and facing the lumen. These covered cantilevers no longer contact flowing blood in the lumen and are not functional to detect flowing blood. The exemplary systems described herein can detect this change in the cantilever environment. For example, a reduction in transmitted signal to a remote receiving device can indicate a covered cantilever and a loss of signal from the sensor device comprising the covered cantilever. Similarly, a reduction in signal due to a reduction in access of the sensor to biomolecules in the lumen can be used to indicate endothelialization. In other embodiments, presence of cells due to endothelialization of the sensor's surface is detected. In some embodiments, the information obtained from one or more sensor can be used to determine or monitor the presence or absence or extent of stent exposure to flowing blood in the lumen of the subject's vessel.

In one embodiment, the sensor is incorporated on the luminal side of the stent struts (towards the lumen of the vessel). This allows the cantilevers of the sensor to respond to changes in the blood flow. In another embodiment, the sensor does not protrude into the blood flow stream. The pressure or capacitive sensors are configured in a flat plane which is approximately parallel to the stent surface.

A piezoelectric cantilever pressure sensor protruding into the lumen of the blood vessel and facing the blood flow can be utilized for detection of endothelialization. An example of such a sensor for detecting the flow of liquid was described in Quist A, et al. "Piezoresistive cantilever based nanoflow and viscosity sensor for micro channels. Lab Chip, Vol. 6, page 1450 (2006).

An exemplary sensor can be attached to an intra-coronary stent, and can be incorporated into the structure of the stent struts in such a manner that the sensor faces the lumen of the vessel and is thus exposed to the flow of blood inside the vessel. The cantilever can be placed vertically from the stent wall or horizontally. The cantilever can be made of silicon or other materials (such as carbon nanotubes) which cause a noticeable change in electrical resistance when bent due to the blood flow. The stent can then be implanted as usual.

Heat Dissipation Rate Sensors

In another embodiment, the sensor is a heat dissipation rate detector utilized for the detection of the degree (extent) of, or the presence/absence of, endothelialization on the interior stent surface. At least one of each of a local heater and a local temperature sensor are mounted on the interior surface of the stent preferably facing the lumen. The heater can be resistively heated (e.g., using the captured energy supplied by the magnetic or RF radiation coming from the outside controller module), or can be directly heated by the radiation itself by inductive means. The heater can also be heated by optical beams such as infrared laser irradiation from a controller module.

The temperature sensor, for example, a controlled thermocouple, can read either the rate of temperature rise during heating or the rate of temperature decay during cooling once the heating is cut off. In one embodiment, an endothelialized stent is covered by endothelial cells and has a reduced heat conduction rate as compared to a stent surface which has delayed endothelialization with passing blood stream rapidly cooling the heated temperature sensor.

Electrical Resistance Sensors

In another embodiment, the detector device includes two or more sensors placed on the surface of the medical device and measures changes in the electrical resistance between these sensors. A change in the resistance between two physically and electrically isolated spots on the stent surface can be utilized for detection of endothelialization. In one embodiment, the electrical resistance measured through endothelialized cells is higher than in the case of a non-endothelialized environment in which the interrogating electrical current pulse encounters less resistance through the blood environment.

Figure 4:
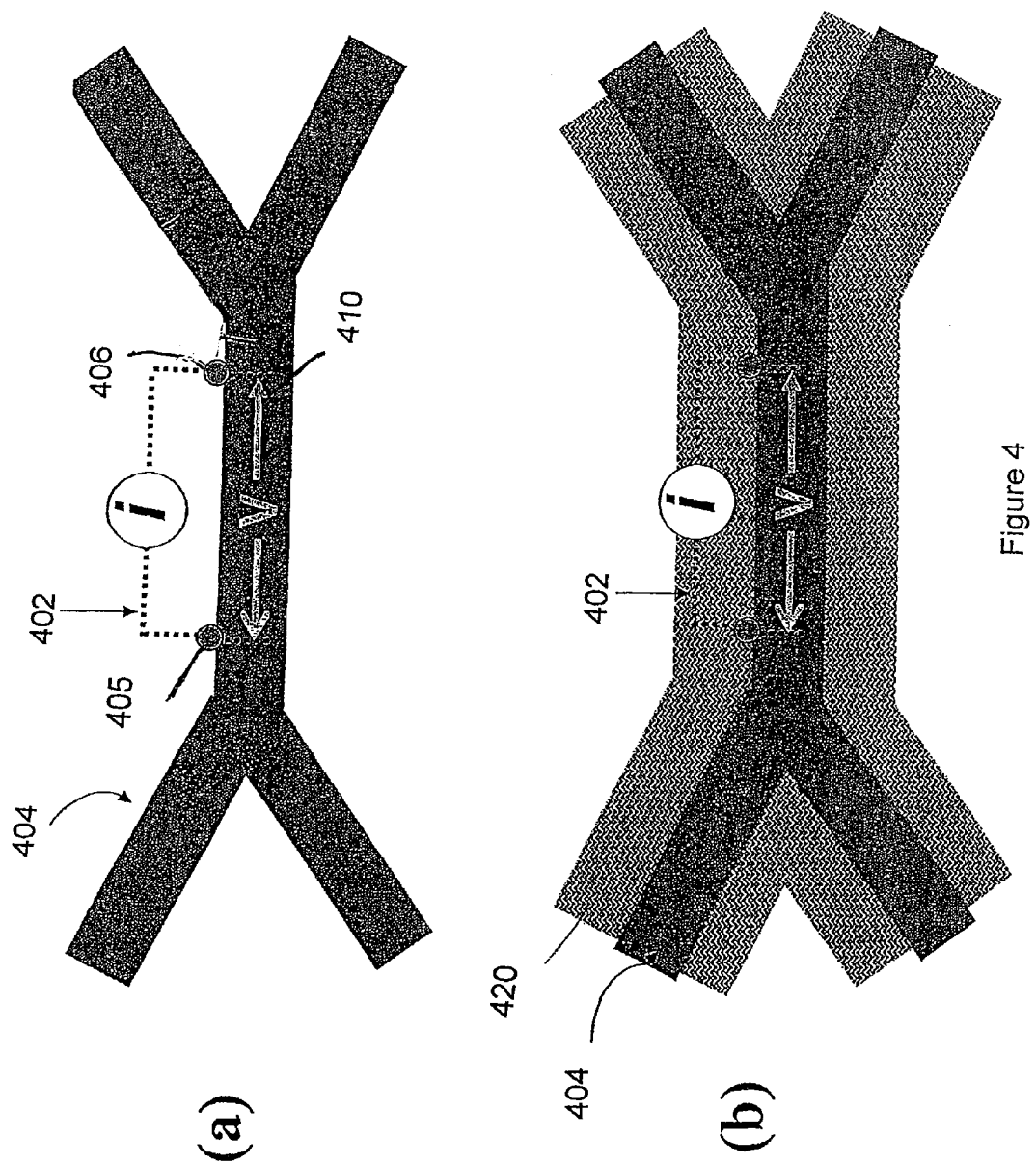
FIGS. 4(a) and 4(b) are schematic diagrams illustrating an electrical resistance measurement system for detection or measurement of endothelialization.

FIGS. 4(a) and (b) are schematic diagrams illustrating an electrical resistance measurement system for detection or measurement of endothelialization. FIG. 4(a) shows sensors 405 and 406 positioned on strut 410 of stent 404. In FIG. 4(a) endothelialization has not occurred on the surface of strut 410. Application of a voltage V between sensors results in a current i (402) flowing through the blood between the sensors. FIG. 4(b) shows stent 404 after endothelialization layer 420 has coated the surface of the stent. A change in the magnitude of current 402 is indicative of endothelialization of the surface.

Magnetostrictive Sensors

In another embodiment, the detection device includes a magnetostrictive sensor which detects changes in magnetization caused by compressive stress induced by either endothelialization cell growth or the heart beat-related change in blood flow pressure on the sensor. Such changes can be utilized for sensing of the degree or presence of endothelialization on the surface of the medical device. In this embodiment, the detection device interfaces with a controller module including a means of supplying a DC or AC magnetic field and a means of measuring the M-H hysteresis or associated changes in magnetic properties. Alternatively, a stress-sensitive magnetoresistance sensor (MR sensor) can also be utilized.

Biomolecular Sensors

In another embodiment, the detection device includes a biomolecule sensor which detects a parameter such as sugar level, ionic contents, oxygen contents, or any exogenous or endogenous intravascular biological property. Such changes can be utilized to evaluate the degree or presence of endothelialization. An example is a micro array electrode oxygen sensors or glucose sensors, which may be powered by captured energy in the sensor circuit via inductive or capacitive coupling.

In one embodiment, a sensor can be used that can act as a receptor/complement with affinity to a labeled nanoparticle that can be injected into the blood stream. When the labeled biocompatible nanoparticles come in contact with the sensor, the predetermined circuit (e.g., electrical conduction path or magnetic circuit) is completed and the RF signal is emitted to the controller module. Once the implantable device is endothelialized, the labeled nanoparticles are not able to come in contact with the sensor, and the circuit is not completed and the RF signal sensor fails to be emitted. Labeled nanoparticles can be injected into a peripheral vein prior to interrogation by a controller module. In this embodiment, labeled nanoparticles act like a switch to turn the circuitry of the sensor "on" prior to being interrogated by the controller module. Exemplary nanoparticle materials includes $Fe_3O_4$ (magnetite) or $Fe_2O_3$ (maghemite) in the desired size regime of ~10 nm or less so that the particles remain superparamagnetic or only slightly ferromagnetic so that they do not magnetically agglomerate. They are semiconducting, however they can be made highly metallic with good electrical conductivity if desired for the endothelialization sensor by inert material coating such as gold or other noble metals. The magnetic oxide nanoparticles are known to be generally biocompatible, and can be eventually filtered and removed by the liver in the human body. The superparamagnetic particles are useful for magnetic MRI testing for enhanced detection signal, for cancer treatment by magnetic hyperthermia. Magnetic nanoparticles are described in Q. A. Pankhurst et al, "Topical Review—Applications of Magnetic Nanoparticles in Biomedicine". J. Phys. D: Appl. Phys. Vol. 36, page R167-R181 (2003).

Infrared Radiation (IR) Based Thermoelectric Sensors

In another embodiment, the detection device includes an infrared radiation based thermoelectric sensor. In this embodiment, an IR absorbing layer such as a gold layer is deposited on a portion of the medical device surface and is utilized to preferentially absorb IR or laser light with a certain frequency, thus creating a temperature gradient. The induced temperature gradient in turn generates a thermoelectric voltage that can be transmitted remotely using the RF circuit to the outside controller module. The endothelialized regions have less heat loss than the non-endothelialized, blood flow region, which give less heat dissipating rate and correspondingly less thermoelectric voltage decay rate than in the blood stream.

Sensor Arrays

Figure 5:
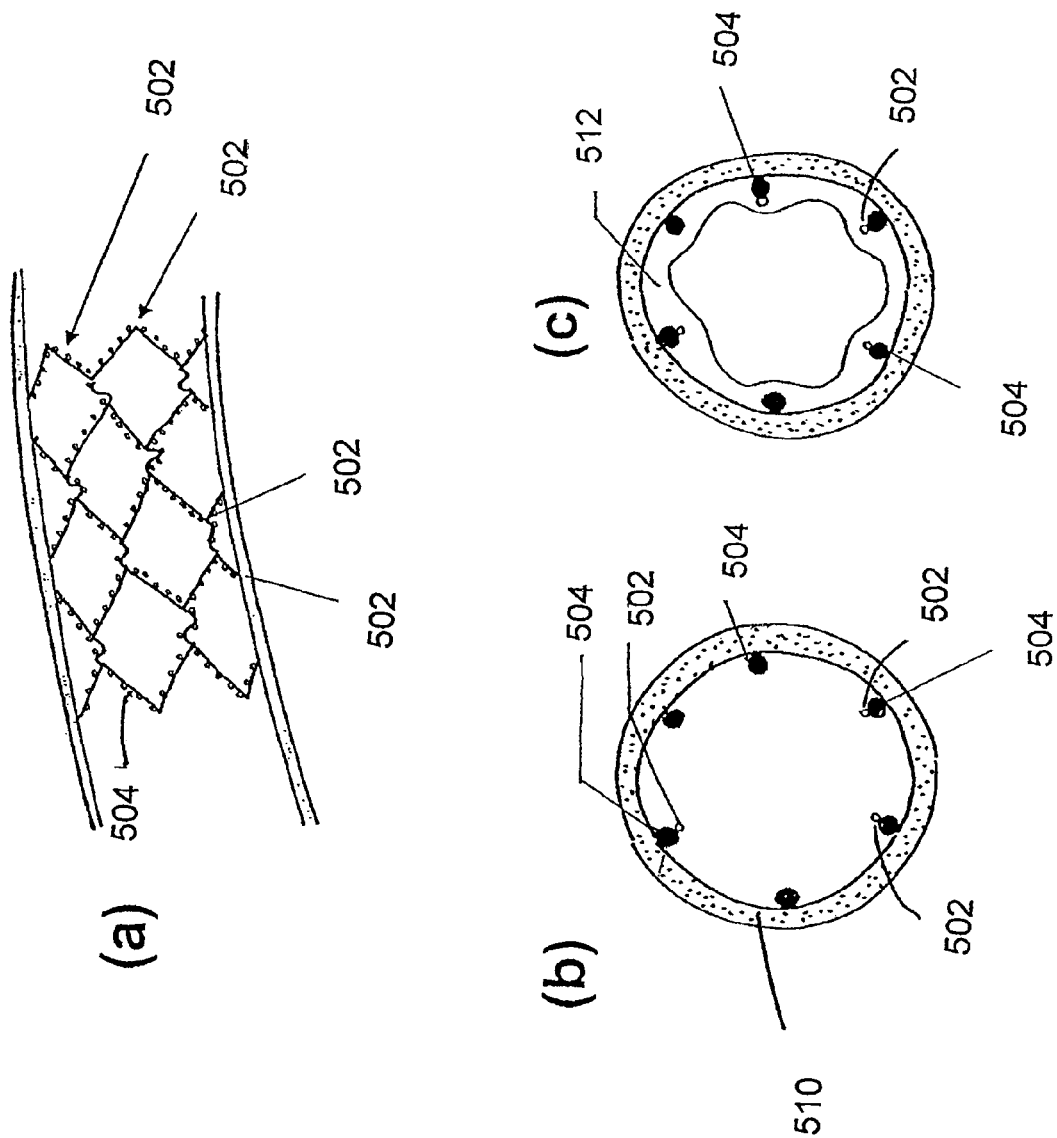
FIGS. 5(a) to 5(c) are schematic diagrams illustrating one distribution of sensors on the surface of a stent.

In one embodiment, a plurality or an array of such sensors, for example, piezoresistive cantilever sensors, are utilized for more accurate measurement of the degree of endothelialization at different portions of the stent. One such distribution of the sensors is illustrated in FIGS. 5(a-c). FIG. 5(a) shows a side view illustrating a plurality of sensors 502 positioned on struts 504 of an expandable stent. FIG. 5(b) shows a cross sectional view showing multiple sensors 502 on struts 504, which are positioned against vessel wall 510. In FIG. 5(b), endothelialization is not present on the surface of struts 504. FIG. 5(c) shows a cross sectional view where the surface of struts 504 are covered by an endothelialization layer 512.

In one embodiment, different sensors are designed to give a different characteristic signal output, for example, different wavelengths of output signals, so that one can detect what portion of the stent has not yet endothelialized. For example, after stent deployment, an output including signals from all or most of the sensors suggests a multitude of sensors exposed, i.e. not covered with an endothelial layer. When the medical device is partially endothelialized, a change in the signal from a portion of the sensors is detected. Complete endothelialization is indicated by a change in the output signal from most or all of the sensors. In certain embodiments, the detection device is capable of detecting stent exposure (i.e. absence of endothelialization) of 1%, 2%, 3%, 4%, 5%, 6%, 7%, 8%, 9%, 10%, 15%, 20%, 30%, 40%, 50%, 60%, 70%, 80%, 90% or 99% of the surface of the medical device. In one embodiment, multiple sensors are positioned evenly over the luminal surface of the medical device. In other embodiments, there is an uneven distribution of sensors. In one embodiment, more sensors are positioned at the ends of the medical device. In another embodiment, more sensors are positioned near the center of the device.

Figure 6:
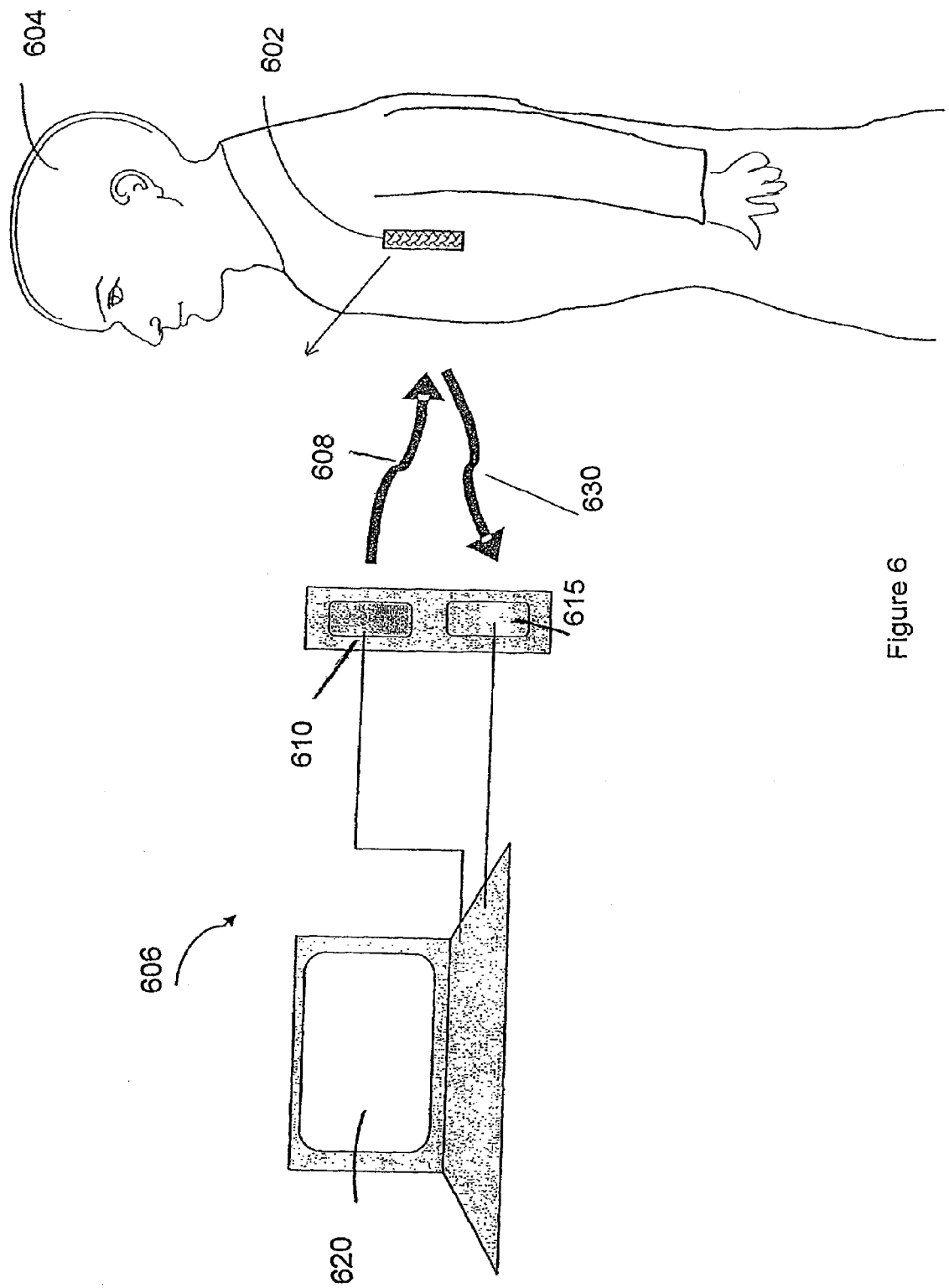
FIG. 6 is a schematic diagram illustrating a system for detecting endothelialization of a surface of a medical device implanted within a vascular system of a patient.

Systems for Detecting Endothelialization of a Surface of an Implanted Medical Device Another aspect provides a system for detecting endothelialization of a surface of a medical device implanted within a vascular system of a patient. FIG. 6 is a schematic diagram illustrating aspects of one embodiment of such as system. The system includes a stent 602 including an operatively associated detection device implanted within a vessel of a subject 604. The detection device is configured to communicate remotely with a base unit 606 for determining the presence or degree of stent endothelialization. In certain embodiments, the base unit includes processing system 620, transmitting system 610 and receiving system 615. In one embodiment, processing system 620, transmitting system 610 and receiving system 615 are integrated into a single unit. In other embodiment, at least one of these components is separate but operatively connected to the other components.

In one embodiment, interrogation signal 608 is used to interrogate the detection device contained in stent 602 when this device is implanted in the subject. In response, sensor signal 630 is transmitted from the detection device associated with stent 602 and is detected by receiving system 615.

In certain embodiments, the interrogation signal 608 and/or sensor signal 630 is a radio frequency signal (RF), a thermal, light, or magnetic signal. Transmitting system 610 can periodically or intermittently send interrogation signal 608 to the implanted detection device. In certain embodiments, interrogation signal 608 and/or sensor signal 630 are radio frequency signals having a frequency within the range 100 KHz to 500 MHz. In other embodiments, magnetic signals having a frequency within the range DC-300 MHz are utilized. Thermal signal can be in the form of laser pulses or a broad-spectrum light, preferably close to the infrared regime for the purpose of enhanced penetration of intended heat through the human tissue toward the sensor or power storage device on the implanted sensor. The form of interrogation signal 608 and sensor signal 630 can be the same, for example, both can be radio frequency signals, or be different.

Sensor signal 630 is transmitted from the detection device associated with stent 602 and is detected by receiving system 615.

Methods of Use

Current medical belief is that the major risk of stent thrombosis persists so long as the stent is not fully endothelialized. A further aspect provides methods which can be used to determine the presence or degree of stent exposure to flowing blood, i.e. incomplete or delayed endothelialization.

One embodiment provides a method for detecting or monitoring endothelialization involving inserting into a subject an implantable medical device having a device for the detection of endothelialization. In one embodiment, the method for detecting or monitoring endothelialization can include determining the presence or absence of device exposure to flowing blood in a subject having the device implanted in a vessel. In one embodiment, the vessel is a coronary vessel. In other embodiments, the vessel is a peripheral vessel. In one embodiment, the implantable medical device is a vascular stent. The stent may or may not be coated with a therapeutic drug. In certain embodiments, the stent is a base metal stent. In other embodiments, the stent is coated with a therapeutic drug for the reduction of the accumulation of cells around the surface of the stent.

In another embodiment, the degree of endothelialization of the surface of the medical device is determined by monitoring the signal from a single sensor. In other embodiments, multiple sensors are monitored to allow for determination of the percentage of endothelialization of the device surface.

In certain embodiments, a percentage value of device exposure (i.e. absence of endothelialization) of about 1% or more at about one month or more after implantation can be used to indicate delayed stent endothelialization. In other embodiments, a percentage value of stent exposure of about 10% or more at about six months after implantation indicates delayed stent endothelialization. In other examples, a percentage value of stent exposure selected from the group consisting of about 2%, 3%, 4%, 5%, 6%, 7%, 8%, 9%, 10%, 15%, 20%, 30%, 40%, 50%, 60%, 70%, or more at about one month, two months, three months, four months, six months, seven months, eight months, nine months, ten months, eleven months, one year, two years or more after implantation can be used to indicate delayed stent endothelialization.

The monitoring process can be performed once or at multiple predetermined times following implantation of the stent sensor device. For example, the monitoring can be performed at about one month or longer following implantation of the stent device into the subject. In one embodiment, the monitoring process can be performed at least once during a time period from about one month following implantation of the stent device to about two years following implantation of the stent device. In another aspect, the monitoring process can be performed at least once at about one year or longer following implantation of the stent. At the time of monitoring, the presence of stent exposure can indicate delayed endothelialization of the stent device. At any time period, the received signal can also be processed to determine the extent of stent exposure.

In other embodiments, the present methods are used in conjunction with drug therapy. In order to prevent the aggregation of platelets onto a metallic stent and thereby initiate the formation of a blood clot, current accepted medical practice is to institute dual antiplatelet therapy comprised of Aspirin and Clopidogrel (such as Plavix® from Sanofi-Aventis, Bridgewater, N.J.). Current practice guidelines recommend preferably one year of dual antiplatelet therapy after DES treatment since it is believed that a stent would be fully endothelialized by this time (see S. C. Smith, Jr, T. E. Feldman, J. W. Hirshfeld, Jr, et al. ACC/AHA/SCAI "2005 guideline update for percutaneous coronary intervention-summary article: a report of the American College of Cardiology/American Heart Association Task Force on Practice Guidelines" (ACC/AHA/SCAI Writing Committee to Update the 2001 Guidelines for Percutaneous Coronary Intervention). Circulation Vol. 113, page 156-175 (2006).

Prolonged antiplatelet therapy with Clopidogrel or other antiplatelet drugs not only puts patients at an increased risk of bleeding, such as during an unforeseen surgical procedure, but is also a substantial financial burden. In addition, concern about LST beyond one year of dual antiplatelet therapy is prompting many patients and their physicians to continue this treatment even at the end of one year.

In one embodiment, the disclosed methods, devices and systems allow for evaluation of the status of endothelialization of such stents. The disclosed methods, devices and systems can be used to more accurately determine medically appropriate times to discontinue the use of expensive and potentially harmful antiplatelet therapy when the stents are endothelialized. Moreover, patients awaiting a surgical procedure can be advised about their peri-operative LST risk, should antiplatelet therapy be discontinued prior to surgery. Therefore, the methods, devices and systems provide a non-invasive evaluation of the "endothelialization status" of the implanted stents.

Further provided is a method for preventing late stent thrombosis (LST) in a subject having a stent device implanted in a vessel and undergoing antiplatelet therapy. In one embodiment, the method comprises detecting the presence or degree of endothelialization of a stent in the vessel using a sensor device implanted within the subject in operative communication with the stent. The presence of stent exposure can be used in the prevention of late stent thrombosis by indicating that antiplatelet therapy is to be maintained in the subject.

Patients who receive stent sensor devices and systems as described herein can optionally begin dual antiplatelet therapy as currently practiced for DES or bare metal stents. These patients can undergo non-invasive testing on clinical follow-up visits to look for signals from the endothelialization sensors. It is expected that these signals will diminish in the ensuing months as the stent struts are gradually endothelialized. A complete lack of generation of these signals, or decrease below a threshold value signals a state of complete endothelialization of the stent or a lack of stent exposure of the stent struts or surfaces to flowing blood. This information can be used to manage any further dual antiplatelet therapy in a given patient. In addition, the described stent sensor device and systems can be used for animal and clinical research to study the time course of endothelialization of stents.

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

What is claimed is:

1. An implantable medical device having components for detecting the degree of endothelialization on a surface of the device, the device comprising:
   (a) a radially-expandable body having a lumen, and
   (b) a detection and transmitting device attached to the lumen, the detection device comprising:
      (i) a sensor positioned on the luminal surface, wherein the sensor is configured on the luminal surface to measure the degree of endothelialization of the luminal surface, and the sensor comprises at least two electrodes positioned apart on the luminal surface, and a signal from the sensor by a transmitter is dependent upon the electrical resistance or electrical capacitance between the two electrodes;
      (ii) a transmitter coupled to the sensor and configured to transmit a signal from the sensor,
   wherein the transmitter transmits signals originating from the at least two electrodes, wherein the signals are dependent upon the electrical resistance or electrical capacitance between the at least two electrodes, and a change in the electrical resistance or electrical capacitance between the two electrodes provides a measure of the degree of endothelialization,
   wherein electrical resistance measured through endothelialized cells is higher than in the case of a non-endothelialized environment in which the interrogating electrical current pulse encounters less resistance through the blood environment; and
      (iii) a receiver coupled to the sensor and a radio frequency transmitter configured to provide electrical power to the detection device from a radio frequency received from an external power source.

2. The implantable medical device of claim 1, wherein the detection device comprises at least two sensors positioned on a luminal surface of the radially-expandable body configured to detect the degree of endothelialization of the surface of the detection device, and wherein the transmitter is configured to transmit a signal from each of the at least two sensors.

3. The implantable medical device of claim 2, wherein the at least two sensors are
   piezoresistive cantilever sensors, each comprising an electrode, and the degree of endothelialization is detected by measuring electrical resistance or electrical capacitance between the at least two electrodes.

4. The implantable medical device of claim 1, wherein the radially-expandable body comprises a material selected from the group consisting of stainless steel, nickel, silver, platinum, gold, titanium, tantalum, iridium, tungsten, and a self-expanding nickel titanium alloy.

5. The implantable medical device of claim 1, wherein the sensor is a heat dissipation rate detector utilized for the detection of the degree of endothelialization.

6. The implantable medical device of claim 1, wherein the sensor is a temperature sensor or a controlled thermocouple, optionally which can read either the rate of temperature rise during heating or the rate of temperature decay during cooling once a heating is cut off,
   wherein optionally an endothelialized stent is covered by endothelial cells and has a reduced heat conduction rate as compared to a stent surface which has delayed endothelialization with passing blood stream rapidly cooling the heated temperature.

7. The implantable medical device of claim 1, further comprising a biomolecule sensor which detects a sugar level, ionic contents, or oxygen contents or any exogenous or endogenous intravascular biological property.

8. The implantable medical device of claim 1, wherein the implantable medical device is a vascular stent, an arterial stent or a venous stent, or a coronary stent.

9. The implantable medical device of claim 1, wherein the implantable medical device comprises: a carbon or a carbon fiber; a cellulose acetate, a cellulose nitrate, a silicone, a polyethylene teraphthalate, a polyurethane, a polyamide, a polyester, a polyorthoester, a polyanhydride, a polyether sulfone, a polycarbonate, a polypropylene, a high molecular weight polyethylene, a polytetrafluoroethylene or a biocompatible polymeric material, or a mixture or a copolymer thereof, a polylactic acid, a polyglycolic acid or a copolymer thereof, a polyanhydride, a polycaprolactone, a polyhydroxybutyrate valerate or a biodegradable polymer or a mixture or a copolymer thereof, a protein, a biologic agent, an extracellular matrix component, a collagen, a fibrin or a mixture or a combination thereof.

10. The implantable medical device of claim 6, wherein the heater can be resistively heated.

11. The implantable medical device of claim 10, wherein the heater can be resistively heated using captured energy supplied by a magnetic or an RF radiation coming from an outside controller module, or optionally the heater can be directly heated by a radiation by inductive means, or optionally the heater can be heated by optical beams, wherein optionally the optical beams comprise infrared laser irradiation from a controller module.

12. A system for detecting the degree of endothelialization of a surface of a medical device implanted within a vascular system of a patient, the system comprising:
   (a) a medical device as set forth in claim 1, and
   (b) a base unit comprising:
      (i) a base unit transmitter configured to transmit a signal to the receiver, wherein the signal is of sufficient strength to provide electrical power to the detection device,
      (ii) a base unit receiver configured to receive a signal from the transmitter, and a base unit processor configured to process the received signal from the transmitter.

13. The system of claim 12, wherein the base unit transmitter is a radio frequency transmitter.

* * * * *